United States Patent [19]

Park et al.

[11] Patent Number: 5,746,972
[45] Date of Patent: May 5, 1998

[54] COMPOSITIONS AND METHODS FOR DISINFECTING AND CLEANING CONTACT LENSES

[75] Inventors: John Y. Park, Santa Ana; Larry K. Thomas, Irvine; Lin Peng, Sunnyvale; Daniel P. Cafaro, Walnut Creek, all of Calif.

[73] Assignee: Allergan, Waco, Tex.

[21] Appl. No.: 742,356

[22] Filed: Nov. 1, 1996

[51] Int. Cl.⁶ .................................. A61L 2/18; C12N 9/08
[52] U.S. Cl. ...................... 422/30; 422/29; 435/192; 435/264; 514/840
[58] Field of Search .................... 422/28, 29, 30; 435/264, 192; 514/839, 840

[56] References Cited

U.S. PATENT DOCUMENTS

| | | | |
|---|---|---|---|
| 3,954,644 | 5/1976 | Krezanoski et al. | 134/3 X |
| 4,568,517 | 2/1986 | Kaspar et al. | |
| 4,767,559 | 8/1988 | Kruse et al. | |
| 4,775,424 | 10/1988 | Wisotzki et al. | 134/42 |
| 5,145,644 | 9/1992 | Park et al. | 422/28 |
| 5,364,601 | 11/1994 | Salpekar. | |
| 5,521,091 | 5/1996 | Cook et al. | 422/30 X |
| 5,589,387 | 12/1996 | Cafaro | 422/28 X |

FOREIGN PATENT DOCUMENTS 9501414  1/1995  WIPO.

OTHER PUBLICATIONS

Ash et al., Handbook of Cosmetic and Personal Care Additives, p. 357, 1994.
BASF, Technical Bulletin on Pluronic F68 Block Copolymer Surfactant (1991).
BASF Performance Chemicals Pluronic & Tetronic Surfactants (1996).
BASF Performance Chemicals (1995).

*Primary Examiner*—Timothy McMahon
*Assistant Examiner*—E. Leigh Dawson
*Attorney, Agent, or Firm*—Frank J. Uxa

[57] ABSTRACT

Compositions and methods for disinfecting and cleaning contact lenses include a liquid medium containing hydrogen peroxide and a defined ethylene oxide/propylene oxide block copolymer. An advantageously reduced amount of foaming occurs when the hydrogen peroxide is destroyed, particularly by the action of catalase.

17 Claims, No Drawings

COMPOSITIONS AND METHODS FOR DISINFECTING AND CLEANING CONTACT LENSES

BACKGROUND OF THE INVENTION

This invention relates to compositions and methods for disinfecting contact lenses. More particularly, the invention relates to compositions and methods adapted for disinfecting and cleaning a contact lens in a single step so that the treated lens can be placed in the eye of a human being for safe and comfortable wear.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

The inclusion of lipid removing agents, such as surfactants, and/or lubricants would provide further benefits, for example, in terms of cleaning performance and convenience, and comfort to the contact lens wearers, to a hydrogen peroxide-based contact lens disinfection system. However, the addition of a surfactant and lubricant to such a system has been difficult and/or has resulted in problems during system use. For example, the presence of surfactants has been known to result in excessive foam generation, for example, during the time catalase is being used to cause the destruction of the hydrogen peroxide.

Therefore, it would be advantageous to provide contact lens disinfection systems which overcome one or more of these problems.

SUMMARY OF THE INVENTION

New systems and methods for disinfecting contact lenses have been discovered. The present systems and methods provide for effective contact lens disinfection, while enhancing removal of lipids and other deposit material from the contact lens and overcoming one or more of the problems noted above. The present invention employs a surfactant component, and preferably a lubricant component, in combination with a contact lens disinfecting amount of hydrogen peroxide. It has been unexpectedly found that a certain class of surfactant components can be included or released in the hydrogen peroxide-containing liquid medium to effectively remove deposit material from a contact lens immersed in the composition and does not result in excessive foam generation. Because the present methods often involve a single user activated step, the user can very easily and effectively employ the present invention to achieve the benefits desired.

In one broad aspect of the present invention, compositions are provided which comprise a liquid medium containing hydrogen peroxide in an amount effective to disinfect a contact lens immersed in the composition; and a surfactant component in an amount effective to remove deposit material from a contact lens immersed in the composition. The surfactant component is selected from block copolymers of ethylene oxide and propylene oxide which include at least about 70% by weight of ethylene oxide units and mixtures thereof. Preferably, the block copolymers have a molecular weight in the range of about 6,000 to about 12,000 daltons. It has been found that the present compositions advantageously generate a reduced amount of foam when subjected to the action of catalase to cause the destruction of the hydrogen peroxide relative to a substantially identical composition in which the surfactant component is replaced by a copolymer component selected from block copolymers of ethylene oxide units and propylene oxide which include 50% by weight or less of ethylene oxide and mixtures thereof. This is indeed surprising since block copolymers having less than 50% by weight of ethylene oxide units have been identified by one manufacturer of such block copolymers as having the best anti-foaming properties.

A particularly useful class of ethylene oxide/propylene oxide block copolymers are those which include at least about 80% by weight of ethylene oxide units.

The amount of hydrogen peroxide, of course, should be sufficient to disinfect a contact lens immersed in the composition. The amount of hydrogen peroxide present in the liquid media useful in the present invention preferably ranges from about 0.5% to about 6% (w/v). It is more preferred that the hydrogen peroxide be present in an amount of about 2.0w (w/v) or less. A somewhat reduced amount of hydrogen peroxide, as noted above, has been found to be useful in further reducing the amount of foam generation obtained when the composition is subjected to the action of catalase to cause the destruction of the hydrogen peroxide.

In one useful embodiment, the present compositions further comprise an effective amount of a lubricant component. Although any suitable lubricant component may be employed, a preferred lubricant component is selected from carboxymethyl celluloses and mixtures thereof. Such carboxymethyl celluloses are effective as lubricants and, preferably, also act to inhibit the formation of deposit material on a contact lens immersed in the composition.

In another aspect of the present invention, compositions, preferably solid compositions, are provided and are useful in disinfecting, and preferably cleaning, contact lenses. Such compositions comprise a catalase component in an amount effective to cause the destruction of hydrogen peroxide in a liquid medium used to disinfect a contact lens, and a surfactant component in an amount effective to remove deposit material from the contact lens in the liquid medium. The surfactant component is selected as set forth elsewhere herein. In a particularly useful embodiment, the compositions further comprise a barrier component in an amount effective to delay the release of the catalase component in a liquid medium for a period of time after the composition is introduced into the liquid medium. This delayed release period of time preferably is sufficiently long to allow a contact lens, which is initially contacted with the liquid medium at substantially the same time as the composition, to be disinfected prior to the release of the catalase component in the liquid medium.

These compositions preferably are such that when they are released in a hydrogen peroxide-containing liquid medium to cause the destruction of the hydrogen peroxide a reduced amount of foam is generated relative to employing a substantially identical composition in which the surfactant component is replaced by a copolymer component selected from a block copolymer of ethylene oxide and propylene oxide which includes 50% by weight or less of ethylene oxide units and mixtures thereof.

The present compositions may further comprise an effective amount of a lubricant composition, as described elsewhere herein.

In addition, the compositions may further comprise an enzyme component effective to remove deposit material from a contact lens in an amount effective to remove deposit material from a contact lens located in a liquid medium in which the enzyme component is released.

In another broad aspect of the present invention, methods for disinfecting a contact lens are provided. Such methods comprise contacting a contact lens with a liquid medium containing hydrogen peroxide in an amount effective to disinfect the contact lens and a surfactant component in an amount effective to remove deposit material from the contact lens at effective contact lens disinfecting conditions to thereby disinfect the contact lens. The surfactant component is selected as set forth elsewhere herein. A catalase component is released in the liquid medium at conditions effective to cause the destruction of hydrogen peroxide in the liquid medium. The present methods preferably generate a reduced amount of foam relative to substantially identical methods in which the surfactant component is replaced by a copolymer component selected from the group consisting of block copolymers of ethylene oxide and propylene oxide which include 50% by weight or less of ethylene oxide units and mixtures thereof.

In still another aspect of the present invention, methods of disinfecting a contact lens are provided which comprise contacting a contact lens with a liquid medium containing hydrogen peroxide in an amount effective to disinfect a contact lens at effective contact lens disinfecting conditions to thereby disinfect the contact lens. A surfactant component is released in the liquid medium in an amount effective to remove deposit material from the contact lens at effective contact lens cleaning conditions. The surfactant component is selected as described elsewhere herein. In addition, a catalase component is released into the liquid medium in an amount effective to cause the destruction of hydrogen peroxide in the liquid medium at effective hydrogen peroxide destroying conditions. The surfactant component and catalase component are preferably initially present as a solid composition.

The solid composition preferably further comprises a barrier component in an amount effective to delay the release of the catalase component in the liquid medium for a period of time after the solid composition is introduced into the liquid medium. Preferably, the solid composition is introduced into the liquid medium at substantially the same time the contacting step is initiated. The present methods may further comprise releasing in the liquid medium an enzyme component effective to remove deposit material from the contact lens in an amount effective to remove deposit material from the contact lens at effective contact lens deposit material removing conditions.

These and other aspects and advantages of the present invention will become apparent in the detailed description, examples and claims.

DETAILED DESCRIPTION OF THE INVENTION

The present invention is of value where hydrogen peroxide is used to disinfect all types of lenses, e.g., contact lenses, which are benefitted by periodical disinfecting. Such lenses may be made of any suitable material or combination of materials and may have any suitable configuration not substantially deleteriously affected by the present compositions or the present methods.

In one aspect, the present invention takes advantage of the discovery that combinations of hydrogen peroxide and certain surfactant components can be used together in a combined liquid medium to achieve disinfection of a contact lens, and removal of deposit material for a contact lens without excessive foam generation when the liquid medium is subjected to the action of catalase to cause the destruction of the hydrogen peroxide. Thus, the disinfected contact lens can be removed from this liquid medium, after the hydrogen peroxide has been destroyed, and placed directly in the eye for safe and comfortable wear.

The surfactant component is selected from block copolymers of ethylene oxide and propylene oxide which include at least about 70% by weight, preferably at least about 80% by weight ethylene oxide units and mixtures thereof. The surfactant components useful in the present invention can be obtained commercially from the BASF Corporation under the trade name of Pluronic® surfactants. Such block copolymers can be generally described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol. In the second step of the synthesis, ethylene oxide is added to sandwich this hydrophobe between hydrophile groups where the length of the hydrophile molecules are controlled to constitute between at least about 70% by weight of the final weight of the molecule. Such surfactant components may be represented by the empirical formula

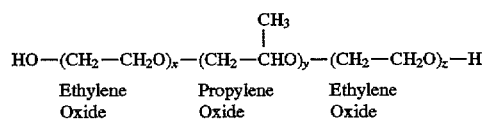

$$HO-(CH_2-CH_2O)_x-(CH_2-\overset{CH_3}{\overset{|}{C}HO})_y-(CH_2-CH_2O)_z-H$$

Ethylene　　　Propylene　　　Ethylene
Oxide　　　　Oxide　　　　　Oxide where each of x, y and z is an independently chosen positive number.

The presently useful surfactant components when not in solution normally exist in solid form.

In accordance with a preferred embodiment of the invention, block copolymers having molecular weights in the range of about 2500 to 13,000 daltons are suitable, with a molecular weight range of about 6000 to about 12,000 daltons being more preferred. Specific examples of Pluronic® surfactants which are satisfactory: F28, F68, F87, F88 and F98. Particularly good results are obtained with Pluronic F-68 surfactant.

A suitable concentration range for the surfactants in order to produce satisfactory deposit material removal is generally about 0.01 to about 10% (w/v) and preferably between about 0.05% or about 0.1% to about 1.0% (w/v).

In the present invention, the hydrogen peroxide is preferably used in the liquid medium in a disinfecting amount. A disinfecting amount preferably means such amount as will reduce the microbial burden by one log order in three hours. More preferably, the amount of hydrogen peroxide used is such that the microbial load is reduced by one log order in one hour. Particularly preferred are those amounts which reduce the microbial load by one log order in 10 minutes or less.

The amount or concentration of hydrogen peroxide may need to be adjusted or controlled to achieve the combination of benefits described herein. For any given surfactant component and concentration of surfactant component routine experimentation can be employed to determine whether or not a given amount of hydrogen peroxide is effective in accordance with the present invention. The amount of hydrogen peroxide present should be sufficient to disinfect a contact lens immersed in the composition. For example, the amount of hydrogen peroxide present in the compositions may be in the range of about 0.5% to about 6% (w/v). Hydrogen peroxide concentrations of about 2% (w/v) or less are particularly useful, for example, in achieving the reduced foam generation benefits of the present invention.

Methods for disinfecting contact lenses are provided. Such methods comprise contacting a contact lens with a liquid medium containing hydrogen peroxide present in an amount effective to disinfect the contact lens. A surfactant component, as described herein, is included in an amount effective to remove deposit material from the contact lens. The hydrogen peroxide-containing liquid medium/contact lens contacting occurs at effective contact lens disinfecting conditions to thereby disinfect the contact lens. A catalase component, preferably present in an amount effective to destroy all the hydrogen peroxide present in the liquid medium, is released in the liquid medium at conditions effective to cause the destruction of hydrogen peroxide in the liquid medium.

The amount of catalase component employed is preferably sufficient to destroy all the hydrogen peroxide present in the liquid medium in which the catalase component is released. Excess amounts of catalase component may be employed. However, very large excesses of catalase component, for example, more than about 300% of the amount needed to destroy all the hydrogen peroxide present in the liquid medium, are to be avoided since such excessive amounts of catalase component may cause problems with the disinfected lens and/or with the ability to safely and comfortably wear such disinfected lens. The catalase component is preferably present in an amount of about 10 to about 1000, more preferably about 20 to about 800, international units of catalase activity per milliliter of liquid medium. The amount of catalase component employed depends not only on the amount of hydrogen peroxide to be destroyed, but also on the specific catalase component being used.

The liquid media in accordance with the present invention are preferably selected to have no substantial detrimental benefit on the lens being treated, and on the wearer of the disinfected lens. The liquid media are constituted to allow, and preferably to even facilitate, contact lens disinfecting. The liquid media are preferably aqueous based and preferably are aqueous, substantially isotonic liquid media. Particularly useful aqueous liquid media are those derived from saline, e.g., a conventional saline solution or buffered saline solution. During the disinfecting contacting, it is preferred that the aqueous liquid medium have a pH in the range of about 2 or 3 to about 9, more preferably about 3 or higher, for example, to about 10, and still more preferably in the range of about 4 or about 5 to about 8. In particular, after all of the hydrogen peroxide has been destroyed, it is preferred that the liquid medium have a pH in the range of about 6 to about 8.

The liquid media, e.g., aqueous liquid media, employed preferably include a buffer component which is present in an amount effective to maintain the pH of the liquid medium in the desired range. This buffer component may be present in the liquid medium, e.g., either separately or in combination with one or more of the other presently useful components, e.g., with the hydrogen peroxide or surfactant component. Among the suitable buffer components or buffering agents which may be employed are those which are conventionally used in contact lens care products. Examples of useful buffer components include those with carbonate functionalities, bicarbonate functionalities, phosphate functionalities, borate functionalities, and the like and mixtures thereof. The buffers may be alkali metal and alkaline earth metal salts, in particular sodium and potassium.

The present compositions preferably include an effective amount of a lubricant component. Such component is effective to provide enhanced comfort to the wearer of the disinfected lens by, for example, effectively conditioning and/or wetting and/or lubricating the lens, during the liquid medium/contact lens contacting. Any suitable lubricant component is useful in the present invention. Examples include various cellulose derivatives, such as hydroxymethyl cellulose, hydroxyethyl cellulose, carboxymethyl cellulose and the like; polyvinyl pyrrolidone; polyvinyl alcohol; and the like and mixtures thereof.

The lubricant component, if present at all, is present in an amount effective to impart or provide enhanced lubricity to the liquid medium. For example, such lubricant component may be included or released in the presently useful liquid medium in amounts similar to the amounts of such lubricant components used in other, e.g., conventional, contact lens care products which include lubricant components. The amount of lubricant component employed preferably is in the range of about 0.01% or about 0.05% to about 0.1% or about 0.5% (w/v) or more.

A particularly useful lubricant component is selected from carboxymethyl celluloses and mixtures thereof. Such materials have been found to effectively delay, or even prevent, deposit formation on the contact lenses treated in accordance with the present invention.

In one embodiment, the catalase component is released on a delayed release basis. For example, catalase component can be present in a single item, i.e., a layered tablet, pill or the like. The item is introduced in a liquid medium containing hydrogen peroxide. After a period of time, e.g., a predetermined period of time for which the item is designed, the catalase component is released in the liquid medium. This causes the destruction of the hydrogen peroxide in the liquid medium.

Tablets, pills, granules or the like which release their ingredients in a sequential, time delayed manner are well known and can be produced using conventional technology. Therefore, a detailed description of such items and such production technology is not presented here. However, such tablets, pills, granules or the like are preferably designed to allow one component sufficient time to perform its function before releasing another component which may interfere with the functioning of the first component. For example, the item is preferably designed to allow the hydrogen peroxide sufficient time to disinfect a contact lens before releasing the catalase component. Such sufficient time is preferably in the range of about 1 minute to about 2 hours, more preferably about 5 minutes to about 1 hour.

Although multi-layered (including core and coating layers) tablets or pills are preferred, the delayed release form of the present catalase component can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Any suitable delayed release component or combination of delayed release components may be employed, provided that such component or components function as described herein and have no substantial detrimental effect on the other components present, on the lens being treated and on the human wearing the treated lens. The delayed release component is preferably at least partially, more preferably completely, water soluble. The delayed release component preferably comprises a major amount of at least one polymeric material. Examples of useful delayed release components include, but are not limited to, soluble cellulose ethers such as methyl cellulose, methylhydroxypropyl cellulose, methylhydroxyethyl cellulose, hydroxypropyl cellulose, hydroxyethyl cellulose and sodium carboxymethyl cellulose; cellulose esters such as cellulose acetate phthalate and hydroxypropylmethyl cellulose phthalate; polymers derived from at least one of acrylic acid, acrylic acid esters, methacrylic acid and methylacrylic acid esters such as methacrylic acid-methyl methacrylate copolymer (for example that sold by Rohm Pharma under the trademark Eudragit L 100) and methacrylic acid-ethyl acrylate copolymers (for example that sold by Rohm Pharma under the trademark Eudragit L 30D); polymers derived from methyl vinyl ether and maleic acid anhydride; polyvinylpyrrolidone; polyvinyl alcohols and the like and mixtures thereof.

In a particularly useful embodiment, at least one enzyme effective to remove debris or deposit material from a contact lens may be employed. Thus, such enzyme or enzymes preferably act in combination with the present surfactant component to effect enhanced deposit material removed from a contact lens contacted with a liquid medium containing these materials. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. The disclosures of these patents are incorporated in their entireties by reference herein. Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the hydrogen peroxide-containing liquid medium to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Keay, L., Moser, P. W. and Wildi, B. S., "Proteases of the Genus Bacillus". II. Alkaline Proteases, "Biotechnology & Bioengineering", Vol. XII, pp. 213–249 (1970, March) and Keay, L. and Moser, P. W., "Differentiation of Alkaline Proteases form Bacillus Species" Biochemical and Biophysical Research Comm., Vol. 34, No. 5, pp. 600–604, (1969).

The subtilisin enzymes are broken down into two subclasses, subtilisin A and subtilisin B. In the subtilisin A grouping are enzymes derived from such species are *B. subtilis, B. liceniformis* and *B. pumilis*. Organisms in this sub-class produce little or not neutral protease or amylase. The subtilisin B. sub-class is made up of enzymes from such organisms a *B. subtilis, B. subtilis var. amylosacchariticus, B. amyloliruefaciens* and *B. subtilis* NRRL B3411. These organisms product neutral proteases and amylases on a level about comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

It is preferred that the lens be contacted with, e.g., immersed in, the liquid medium for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the liquid medium be destroyed in less than about 3 hours or about 4 hours, more preferably in less than about 1 hour and still more preferably in less than about 30 minutes after catalase component is the hydrogen peroxide-containing liquid medium.

The disinfecting contacting preferably occurs in a quantity, e.g., about 5 ml to about 15 ml, of the hydrogen peroxide-containing liquid medium at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to effectively disinfect the lens being treated.

After the contacting and releasing steps, the disinfected lens is preferably taken from the liquid medium and placed directly in the eye for safe and comfortable wear.

Alternately, the disinfected lens can be rinsed, e.g., with saline solution, to free the lens of enzyme or enzymes prior to placing the disinfected lens into the eye.

The following non-limiting examples illustrate certain aspects of the present invention.

EXAMPLE 1

A quantity of the following liquid composition is prepared by blending together the individual ingredients.

| | |
|---|---|
| Buffered saline solution | Q.S. 100% |
| Hydrogen Peroxide | 2% (w/v) |
| Ethylene oxide/propylene oxide block copolymer[1] | 0.2% (w/v) |

[1]Copolymer includes 80% by weight of ethylene oxide units and is sold by BASF under the trademark Pluronic F-68.

EXAMPLE 2

A coated tablet, having a core tablet surrounded by a coating is prepared for testing. The coated tablet is prepared in accordance with the teachings of Park et al U.S. Pat. No. 5,145,644, the disclosure of which is incorporated in its entirety by reference herein. The core tablet has the following composition.

| CORE TABLET: | |
|---|---|
| Crystalline catalase[2] | 1.5 mg |
| Sodium chloride | 89.4 mg |
| Dibasic sodium phosphate (anhydrous) | 12.5 mg |
| Monobasic sodium phosphate monohydrate | 0.87 mg |
| Polyethylene glycol (molecular weight of about 3350) | 1.05 mg |
| COATING: | |
| Hydroxypropylmethyl cellulose | 3 to 6 mg |

[2]The amount of catalase added was determined by an assay of the batch of product to be used. The tablet prepared contained about 5200 units of catalase activity.

EXAMPLE 3

A quantity of 10 ml of the liquid composition of Example 1 is placed in a conventional contact lens vial. A pair of contact lenses are placed in a conventional holder and the holder is placed in the vial so that the lenses are immersed in the composition of Example 1. At substantially the same time, a coated tablet of Example 2 is placed in the vial.

After a period of time, on the order of about 30 minutes, the material in the vial begins to bubble. This indicates that the catalase has been released from the coated tablet in the liquid medium and is causing the destruction of hydrogen peroxide. After about 45 minutes, the bubbling stops. During the time that hydrogen peroxide is being destroyed, substantially no excess foam formation is observed.

It is found that the contact lenses have been disinfected and that deposit material originally present on the lenses have been removed. The lenses are removed from the vial and holder and are placed directly into the eyes of a human being for safe and comfortable wear.

EXAMPLE 4

Example 1 is repeated except that the liquid composition includes 0.05% (w/v) of sodium carboxymethylcellulose.

EXAMPLE 5

Example 3 is repeated except that the composition of Example 4 is used in place of the composition of Example 1. Substantially similar results to those obtained in Example 3 are observed. In addition, the sodium carboxymethylcellulose is found to be an effective lubricant, facilitating the wearing of the disinfected contact lenses by the human being.

EXAMPLE 6

Example 2 is repeated except that the core tablet includes 5 mg. of sodium carboxymethyl cellulose.

EXAMPLE 7

Example 3 is repeated except that the composition of Example 6 is used in place of the composition of Example 2. Substantially similar results to those obtained in Example 3 are observed. In addition, the sodium carboxymethylcellulose is found to be an effective lubricant, facilitating the wearing of the disinfected contact lenses by the human being.

EXAMPLE 8

Example 2 is repeated except that the core tablet includes 20 mg. of the copolymer identified in Example 1.

EXAMPLE 9

Example 3 is repeated except that the composition of Example 8 is used in place of the composition of Example 2 and the liquid composition added to the lens vial initially includes no copolymer. Substantially similar results to those obtained in Example 3 are observed.

EXAMPLE 10

Example 8 is repeated except that the core tablet also includes 5 mg. of sodium carboxymethyl cellulose.

EXAMPLE 11

Example 3 is repeated except that the composition of Example 10 is used in place of the composition of Example 2 and the liquid composition added to the lens vial initially includes no copolymer. Substantially similar results to those obtained in Example 3 are observed. In addition, the sodium carboxymethylcellulose is found to be an effective lubricant, facilitating the wearing of the disinfected contact lenses by the human being.

While this invention has been described with respect to various specific examples and embodiments, it is to be understood that the invention is not limited thereto and that it can be variously practiced within the scope of the following claims.

What is claimed is:

1. A composition comprising:
    a liquid medium containing hydrogen peroxide in an amount of about 2.0% (w/v) or less effective to disinfect a contact lens immersed in said composition; and
    a surfactant component in an amount effective to remove deposit material from a contact lens immersed in said composition, said surfactant component being selected from the group consisting of block copolymers of ethylene oxide and propylene oxide which include at least about 70% by weight of ethylene oxide units and mixtures thereof, said composition generating a reduced amount of foam when subjected to the action of catalase to cause the destruction of the hydrogen peroxide relative to a substantially identical composition in which the surfactant component is replaced by a copolymer component selected from the group consisting of block copolymers of ethylene oxide and propylene oxide which include 50% by weight or less of ethylene oxide units and mixtures thereof.

2. The composition of claim 1 wherein said block copolymers have a molecular weight in the range of about 6,000 to about 12,000 daltons.

3. The composition of claim 1 wherein said block copolymers include at least about 80% by weight of ethylene oxide units.

4. The composition of claim 1 which further comprises an effective amount of a lubricant component.

5. The composition of claim 4 wherein said lubricant component comprises carboxymethyl cellulose.

6. A composition comprising:

a catalase component in an amount effective to cause the destruction of hydrogen peroxide in a liquid medium used to disinfect a contact lens; and a surfactant component in an amount effective to remove deposit material from the contact lens in the liquid medium, said surfactant component being selected from the group consisting of block copolymers of ethylene oxide and propylene oxide which include at least about 70% by weight of ethylene oxide units and mixtures thereof, said composition, when released in a liquid medium containing hydrogen peroxide in an amount of about 2% (w/v) or less to cause the destruction of the hydrogen peroxide, generates a reduced amount of foam relative to a substantially identical composition in which the surfactant component is replaced by a copolymer component selected from the group consisting of block copolymers of ethylene oxide and propylene oxide which include 50% by weight or less of ethylene oxide units and mixtures thereof.

7. The composition of claim 6 which is solid.

8. The composition of claim 6 which further comprises a barrier component in an amount effective to delay the release of said catalase component in a liquid medium for a period of time after said composition is introduced into the liquid medium.

9. The composition of claim 6 wherein said block copolymers include at least about 80% by weight of ethylene oxide units.

10. The composition of claim 6 which further comprises an effective amount of a lubricant component.

11. The composition of claim 10 wherein said lubricant component comprises carboxymethyl cellulose.

12. The composition of claim 6 which further comprises an enzyme component effective to remove deposit material from a contact lens in an amount effective to remove deposit material from a contact lens located in a liquid medium in which said enzyme component is released.

13. A method of disinfecting a contact lens comprising:

(1) contacting a contact lens with a liquid medium containing hydrogen peroxide in an amount effective to disinfect said contact lens and a surfactant component in an amount effective to remove deposit material from said contact lens at effective contact lens disinfecting conditions to thereby disinfect said contact lens, said surfactant component being selected from the group consisting of block copolymers of ethylene oxide and propylene oxide which includes at least about 70% by weight of ethylene oxide units and mixtures thereof; and (2) contacting said liquid medium with a catalase component in an amount effective to cause the destruction of the hydrogen peroxide in said liquid medium, wherein step (2) generates a reduced amount of foam relative to a substantially identical method in which the surfactant component is replaced by a copolymer component selected from the group consisting of block copolymers of ethylene oxide and propylene oxide which include 50% by weight or less of ethylene oxide units and mixtures thereof.

14. The method of claim 13 wherein said liquid medium further contains an effective amount of a lubricant component.

15. The method of claim 14 wherein said lubricant component comprises carboxymethyl cellulose.

16. A method of disinfecting a contact lens comprising:

contacting a contact lens with a liquid medium containing hydrogen peroxide in an amount effective to disinfect said contact lens at effective contact lens disinfecting conditions to thereby disinfect said contact lens;

releasing in said liquid medium a surfactant component in an amount effective to remove deposit material from said contact lens at effective contact lens cleaning conditions, said surfactant component being selected from the group consisting of block copolymers of ethylene oxide and propylene oxide which include at least about 70% by weight of ethylene oxide units and mixtures thereof; and releasing in said liquid medium a catalase component in an amount effective to cause the destruction of hydrogen peroxide in said liquid medium at effective hydrogen peroxide destroying conditions, wherein the release of the catalase component generates a reduced amount of foam relative to a substantially identical method in which the surfactant component is replaced by a copolymer component selected from the group consisting of block copolymers of ethylene oxide and propylene oxide which include 50% by weight or less of ethylene oxide units and mixtures thereof.

17. The method of claim 16, which further comprises releasing an effective amount of a lubricant component comprising carboxymethyl cellulose in said liquid medium.

\* \* \* \* \*